(12) United States Patent
Tarakçi et al.

(10) Patent No.: US 12,274,343 B2
(45) Date of Patent: Apr. 15, 2025

(54) ACTIVITY ANALYSIS SYSTEM USING ADAPTIVE NAIL CLIPPERS

(71) Applicant: ISTANBUL MEDIPOL UNIVERSITESI, Istanbul (TR)

(72) Inventors: Devrim Tarakçi, Istanbul (TR); Havva Münteha Inanici, Istanbul (TR); Kübra Sahadet Sezer, Istanbul (TR)

( * ) Notice: Subject to any disclaimer, the term of this patent is extended or adjusted under 35 U.S.C. 154(b) by 442 days.

(21) Appl. No.: 17/311,853

(22) PCT Filed: Dec. 24, 2019

(86) PCT No.: PCT/TR2019/051199
§ 371 (c)(1),
(2) Date: Jun. 8, 2021

(87) PCT Pub. No.: WO2020/139295
PCT Pub. Date: Jul. 2, 2020

(65) Prior Publication Data
US 2022/0015522 A1 Jan. 20, 2022

(30) Foreign Application Priority Data
Dec. 28, 2018 (TR) .................................. 2018/20987

(51) Int. Cl.
*A45D 29/02* (2006.01)
*A61B 5/00* (2006.01)
(Continued)

(52) U.S. Cl.
CPC .............. *A45D 29/02* (2013.01); *A61B 5/015* (2013.01); *A61B 5/1112* (2013.01);
(Continued)

(58) Field of Classification Search
None
See application file for complete search history.

(56) References Cited

U.S. PATENT DOCUMENTS 6,220,251 B1 * 4/2001 Jeong ..................... A45D 29/18
30/28
8,863,758 B1 * 10/2014 Walenciak ............ B26B 27/007
30/28
(Continued)

FOREIGN PATENT DOCUMENTS

GB 2556973 A 6/2018
KR 20120098538 A 9/2012

OTHER PUBLICATIONS

International Search Report for corresponding PCT/TR2019/051199, dated Apr. 17, 2020.
(Continued)

*Primary Examiner* — Hwei-Siu C Payer
(74) *Attorney, Agent, or Firm* — Egbert, McDaniel & Swartz, PLLC

(57) ABSTRACT

An activity analysis system includes a body with a spring like flexible structure, a light at the tip used for people with low vision, a battery compartment required for the light battery to operate, upper and lower cutting blades performing the nail cutting process, a ring area of the clipper that is required in order to be worn by the finger, a magnifying glass to be installed optionally, a sensor detecting the temperature of the fingers, movements of flexion, extension, rotation, limitations of joints, gripping strength, and sensory mapping of the strength points, a right sensor and a left sensor, a wristband with GPS, a connection element enabling the connection between left and right sensors that are located on the wristband and the sensor on the nail clippers, and a computer which gathers the analysis results obtained from the sensors.

4 Claims, 2 Drawing Sheets

Figure 1:
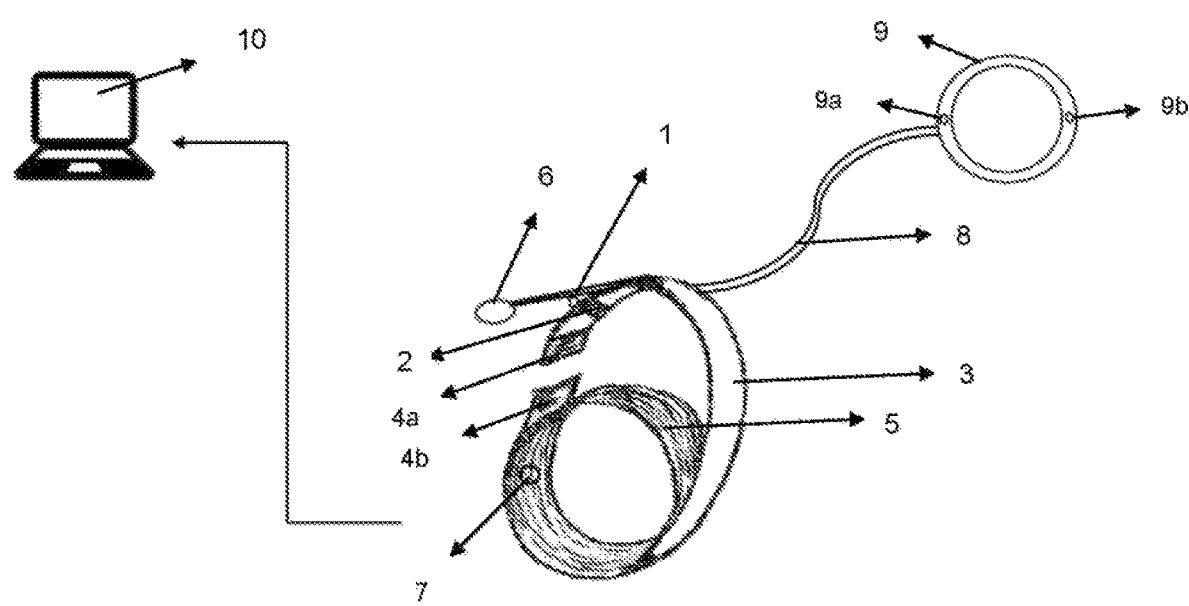

(51) Int. Cl.
*A61B 5/01* (2006.01)
*A61B 5/11* (2006.01)
*A61B 5/22* (2006.01)
*A45D 44/00* (2006.01)

(52) U.S. Cl.
CPC .......... *A61B 5/1121* (2013.01); *A61B 5/1125* (2013.01); *A61B 5/225* (2013.01); *A61B 5/6887* (2013.01); *A45D 2044/007* (2013.01)

(56) References Cited

U.S. PATENT DOCUMENTS

| | | | |
|---|---|---|---|
| 2015/0126873 A1* | 5/2015 | Connor | A61B 5/6887 600/407 |
| 2015/0289823 A1* | 10/2015 | Rack-Gomer | A61B 5/01 600/365 |
| 2015/0305621 A1 | 10/2015 | Khan | |
| 2016/0313798 A1* | 10/2016 | Connor | G06F 3/017 |
| 2017/0055885 A1 | 3/2017 | Shoeb et al. | |
| 2018/0279940 A1 | 10/2018 | Campbell | |
| 2019/0145840 A1* | 5/2019 | Kivioja | G01L 5/0038 73/862.541 |
| 2022/0015522 A1* | 1/2022 | Tarakçi | A61B 5/225 |

OTHER PUBLICATIONS

Written Opinion of the International Searching Authority for corresponding PCT/TR2019/051199, dated Apr. 17, 2020.

* cited by examiner

ACTIVITY ANALYSIS SYSTEM USING ADAPTIVE NAIL CLIPPERS

TECHNICAL FIELD

The invention is related to an adaptive nail clipper usage analysis system which eases the usage for children, adults or elderly, which can measure the difference occurring during activity, can detect finger movements of flexion, extension, and rotation, can detect limitations and range of motion, can create a temperature map and a sensory map, and that can measure gripping strength.

PRIOR ART

Activities of Daily Living (ADLs) are all of the activities that are important for society and that are done by a person every day typically; such as self-care, getting dressed, eating, taking a bath, toilet hygiene, sleeping, house cleaning. Personality traits, age, gender and culture of an individual are among the factors that affect ADL. ADL is analyzed in two groups as Basic Activities of Daily Living (BADL) and Instrumental Activities of Daily Living (IADLs). Self-care activities such as nourishment, taking a bath, getting dressed, going to the toilet are BADL, and activities such as shopping, transportation, managing finances, traveling, preparing food, housework are IADLs.

Nail trimming activity is a self-care activity within daily life activities. There are many factors affecting personal independence in daily life. Neuromuscular diseases, rheumatoid, rheumatoid arthritis, old age, and cancer are among these factors. Progressive muscle weakness, which is present in many neuromuscular diseases, directly affects upper extremity functions. This situation leads to patients having difficulty with distal muscle groups such as taking their hands to their mouths, using knives and forks bilaterally and trimming nails, and in some cases, to inability to perform these activities.

Rheumatoid arthritis is an inflammatory disease that causes progressive destruction in joints, frequently in wrists and hands, affecting many systems, and having an unknown etiology. This disease, which causes a great deal of stress and pressure on joints, affects daily life activities, social activities, home and work environments of individuals.

Pain, swelling and deformities that occur during the course of the disease adversely affect hand functions and as a result, daily life activities are primarily affected. A person who has serious deformations in her/his hands, experiences difficulties in basic activities such as eating, drinking and gripping objects.

Cancer and cancer-related secondary activities have an adverse effect on a person's life while she/he is performing self-care activities. The person cannot perform nail trimming activity due to fatigue and muscle weakness during the progress of this disease. Nail trimming activity is performed with difficulty in elders as well. It is known that visual problems in people with low vision, cause a decrease in independence while performing daily life activities such as self-care, reading, solving arithmetic problems, and driving. In addition, a person may not be able to perform nail trimming activity to the fullest extent due to De Quervain syndrome. Healthy individuals also experience difficulties in stabilizing the nail clipper due to its small size and texture. Difficulties arise during the nail clipping process due to these problems in the present situation.

Nail clippers that are used in the prior art, do not have a universal design for children, adults or elderly to use. Major muscle groups are used in the big joints, minor muscle groups are used in the small joints. It is known that more energy is consumed in activities carried out with small muscle groups. In the prior art, the nail clipper is gripped with the fingertips of the first and the second fingers (with distal phalanx), thus more muscle strength is used, and it is known that stabilizing the nail clippers is difficult. Some of the present nail clippers cannot be held in hand, they are fixed on a table. Only one aspect of the nail clippers is thought while designing nail clippers for people with impaired hand skills. For example, in a model, the clipper is thickened and a handle is mounted accordingly for people with impaired gripping ability.

Activity analysis is formed by analyzing the environment in which the activity is being performed and by analyzing the body functions and structures. Basically, a motor movement consists of a mechanism that receives inputs, communicates them to the somatomotor cortex where the inputs are processed by receptors, and activity is realized via a motor answer. The parameter of activity analysis related to the human body consists of the detection of muscle groups used during the activity, assessing the strength of the detected muscle groups, determining the degree of range of motion of joints and sensory assessments. In the current process, when an activity is desired to be analyzed, the analysis of muscle strength is conducted via a pinch-meter, range of motion of joints is tested via a goniometer and sensory maps are tested via monofilament tests separately. In the prior art, nail clippers do not analyze during activity. They do not measure muscle strength, grip strength, temperature change, give information on joint movements and cannot produce qualitative data regarding the effectiveness of the treatment as being used in the rehabilitation process. It takes a long time to test muscle strength, range of motion of joints, and sensory assessment separately. In the prior art of activity analysis, the therapist monitors the movement as an observer and obtains results by manual assessments. None of the existing known systems is technological. Energy and time will be saved via the technological system during an activity with the invention and sensory and motor parameters will be analyzed objectively. In the current activity analysis process, it is not possible to calculate how much strength is released from which muscle functionally. Muscle strength analysis via pinch-meter measures muscle strength but cannot measure the muscle strength during the activity. Muscle strength during an activity will be measured functionally by means of the invention. In the current activity analysis process, assessments of the therapist do not provide a functional result. The activity analysis system that the invention provides, will enable blade sensory and temperature maps to be created functionally. The credibility of the rehabilitation process will increase through the qualitative and objective data produced by the activity analysis system.

OBJECTIVE AND BRIEF DESCRIPTION OF THE INVENTION

The objective of the invention is to ease, to facilitate the implementation of the nail trimming activity or to increase independence during the nail trimming activity of healthy children, elderly and adults, or of children, elderly and adult who have weak hand skills due to any reason, by providing a universal design which has sensory receptors to conduct analysis during the nail trimming process and to determine whether the individual has limitations to perform activity on the finger and wrist, and to provide quantitative improvement by being used in rehabilitation.

Another aim of the invention is to increase the independence of healthy individuals or elderly, adults and children who have weak hand skills due to any reason, in self-care activities and to save energy by providing a universal and ergonomic design.

Another aim of the invention is to facilitate activities of individuals who have impaired vision by placing a light at the tip of the nail clippers. The magnifying glass, which can be optionally installed on the clipper, makes it easier for people who have visual impairment to see their fingers properly.

By means of the nail clipper of the invention, gripping is facilitated by the 1st and 2nd fingers (with proximal phalanxes) by the usage of a ring section into which the finger is inserted in and stabilization is enabled with the body section which supports the other finger. The user of the clipper can grip with fingers or with other fingers according to preference. The required muscle strength is decreased since the movement is carried out closer to the proximal joint.

Finger and wrist movements of flexion, extension, and rotation, limitations, range of motion, grip strength, temperature, and sensory maps can be detected by the sensors on the wristband that are connected to the sensor placed on the nail clipper. In addition, these activities can be logged onto a computer via GPS on the wristband.

In an embodiment, the invention has sensors that can measure the temperature during activity and that can map user temperature. Measured temperature data will be helpful for the therapist in mapping the sensory pressure used by the patient. Activity Analysis can be conducted with the help of the muscle movements detected by the sensors. Adaptive nail clippers can also be used as a quantitative assessment and measurement tool that shows the effectiveness of treatment.

All the advantages, characteristics and structural properties of the invention will be better understood by means of the attached figures and detailed description; therefore if an assessment is carried out, it should be done so, by taking into consideration these figures and detailed descriptions.

FIGURES OF THE INVENTION

FIG. 1: Illustration of the activity analysis system using adaptive nail clippers FIG. 2: Overview of the adaptive nail clippers being used on a finger

REFERENCES DESCRIBING THE INVENTION

1. Light
2. Battery compartment
3. Body
4a. Upper cutting blade
4b. Lower cutting blade
5. Ring area
6. Magnifying glass
7. Sensor
8. Connection element
9. Wristband
9a. Right sensor
9b. Left sensor
10. Computer

DESCRIPTION OF THE INVENTION

In this detailed description, the activity analysis system using the adaptive nail clippers is described without limiting the scope of the invention.

The invention consists of; a body (3) with a spring like flexible structure, a light (1) at the tip used for people with low vision, battery compartment (2) required for the light (1) battery to operate, upper cutting blade (4a) and lower cutting blade (4b) performing the nail cutting process, the ring area (5) of the clipper that is required in order to be worn by the finger, magnifying glass (6) to be installed optionally, sensor (7) detecting the temperature of the fingers, movements of flexion, extension, rotation, limitations of joints, gripping strength, and sensory mapping of the strength points, a right sensor (9a) and a left sensor (9b), a wristband (9) with GPS, a connection element (8) enabling the connection between right and left sensors (9a) (9b) that are located on the wristband and the sensor (7) on the nail clippers, and a computer (10) which gathers the analysis results obtained from the sensors (7) (9a) (9b).

The invention facilitates the independent activity of nail clipping and enables the functional use of fingers during this activity. In the present systems, the movement during the nail clipping is carried out within the distal phalanx of the fingers; by means of the invention, the movement will be performed within proximal phalanx and thereby it reduces the muscle power used, by shortening the force path for the strength needed in biomechanics.

Temperature maps in fingers, movements of flexion, extension, and rotation, limitations, range of motion, grip strength and sensory map of the sensory and strength points are detected by the sensor (7) on the adaptive nail clippers. Wrist movements of flexion, extension, and rotation, limitations, range of motion, grip strength and sensory maps are detected by the right sensor (9a) and left sensor (9b) on the wristband (9). The detected values of the finger are transferred to the GPS on the wristband (9) via the connection element (8). Similarly, the values detected on the wristband are transferred to the GPS on the wristband (9). GPS transfers all the data to the computer (10) environment. All analysis data are collected in a computer (10) environment. By means of the analyzed data, qualitative results for experts are obtained. In addition, the invention can be used as an activity-specific analysis and measurement tool before and after the treatment.

Figure 2:
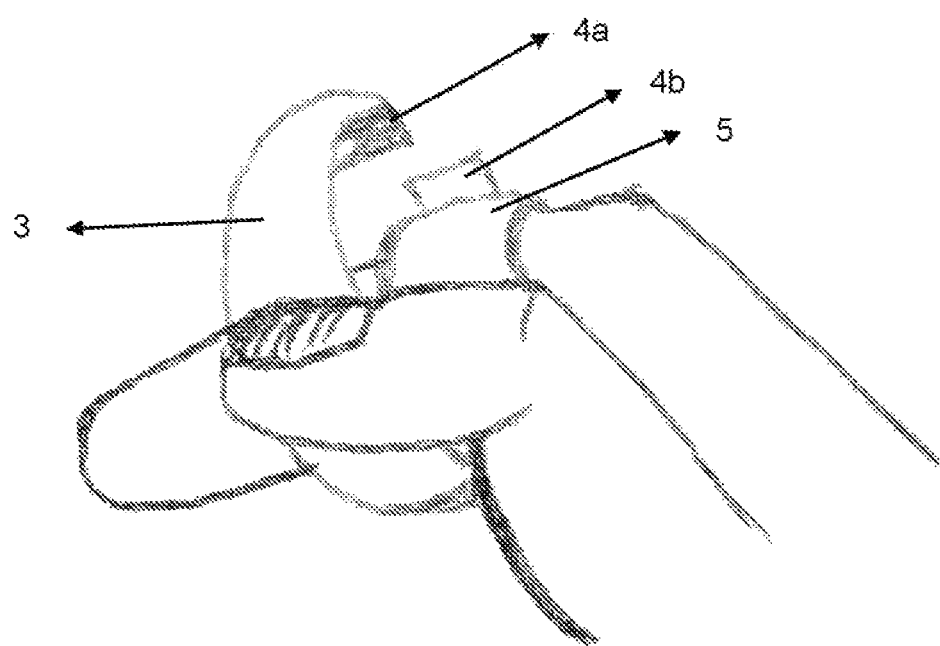

The handling of the nail clippers is facilitated with the ring area (5) of the present invention. As it is seen in FIG. 2, the ring area (5) of the adaptive nail clippers subject to the invention, is placed on the index finger and used only by pressuring the body (3) with the thumb.

Furthermore, the invention is practical for the elderly, adults or children whose activities are impaired for any reason, for people who have difficulties due to their impaired vision, and for people who do not have any health problems but have difficulties in just stabilizing the nail clippers.

The technical and all of the other features referred to in each claim are followed by a reference number which is used only to facilitate understanding of the claims, and therefore should not be construed as limiting the scope of any of the elements indicated by these reference numbers for illustrative purposes.

It is evident that a person skilled in the art can reach the novelty disclosed in the invention using similar embodiments and/or can apply this embodiment to other fields of similar purpose used in the art. It is therefore evident that such embodiments will not meet the novelty criteria and will particularly not meet the criteria of surpassing the prior art.

The invention claimed is:
1. An activity analysis system using adaptive nail clippers, the system comprising:
a body with a flexible structure;

a ring suitable for a finger of a user to be inserted therein, the body extending from the ring, the ring having a sensor thereon;

an upper cutting blade provided on an end of the body;

a lower cutting blade provided on the ring and positioned opposite the upper cutting blade, and the upper cutting blade and the lower cutting blade cooperating with each other for performing a nail clipping process;

a light affixed to the body;

a battery compartment having a battery therein for powering the light;

a wristband with GPS, the wristband having a left sensor and a right sensor thereon;

a connection element extending between the wristband and the body, the connection element adapted to provide a connection between the left and right sensors of the wristband and the sensor on the ring; and a computer in communication with the GPS of the wristband, the computer adapted to receive detected values from the left and right sensors of the wristband and the sensor of the ring.

2. The activity analysis system using adaptive nail clippers of claim 1, further comprising a magnifying glass affixed to the body.

3. The activity analysis system using adaptive nail clippers of claim 1, wherein the sensor of the ring is adapted to detect values associated with the finger of the user.

4. The activity analysis system using adaptive nail clippers of claim 1, wherein the right sensor and the left sensor of the wristband are adapted to detect values associated with a wrist of the user.

* * * * *